United States Patent
Fu et al.

(10) Patent No.: US 7,253,315 B2
(45) Date of Patent: *Aug. 7, 2007

(54) PROCESS FOR PREPARING FLUOROCARBOXYLIC ACIDS

(75) Inventors: Ta-Wei Fu, Vienna, WV (US); Steven H. Swearingen, Wilmington, DE (US); Takuya Ichida, Settsu (JP); Shigeyuki Yoshii, Settsu (JP)

(73) Assignees: Daikin Industries, Ltd., Osaka (JP); E. I. du Pont de Nemours and Company, Wilmington, DE (US)

( * ) Notice: Subject to any disclaimer, the term of this patent is extended or adjusted under 35 U.S.C. 154(b) by 184 days.

This patent is subject to a terminal disclaimer.

(21) Appl. No.: 11/088,370

(22) Filed: Mar. 24, 2005

(65) Prior Publication Data
US 2005/0165254 A1    Jul. 28, 2005

Related U.S. Application Data (63) Continuation of application No. PCT/US2003/026306, filed on Sep. 24, 2003.

(60) Provisional application No. 60/413,154, filed on Sep. 25, 2002.

(51) Int. Cl.
  C07C 53/15    (2006.01)
  C07C 51/58    (2006.01)
(52) U.S. Cl. ..................... 562/602; 562/849
(58) Field of Classification Search ........... 562/602, 562/604, 605
See application file for complete search history.

(56) References Cited

U.S. PATENT DOCUMENTS

| | | | |
|---|---|---|---|
| 3,227,736 A | 1/1966 | Tschesche et al. ....... 260/405.5 |
| 4,400,325 A | 8/1983 | von Werner et al. | |
| 4,927,962 A | * 5/1990 | Aramaki et al. ............. 562/113 |
| 5,196,579 A | 3/1993 | Gries et al. ................. 562/580 |
| 6,013,795 A | 1/2000 | Manzara et al. ............ 544/106 |
| 6,248,923 B1 | 6/2001 | Lin et al. ..................... 562/892 |
| 2003/0171616 A1 | 9/2003 | Watanabe et al. | |

FOREIGN PATENT DOCUMENTS

| | | |
|---|---|---|
| DE | 42 13 641 A1 | 10/1993 |
| EP | 0 510 596 A2 | 10/1992 |
| JP | 06-009487 | 1/1994 |
| JP | 06-128189 | 5/1994 |
| JP | 08-231462 | 10/1996 |
| WO | WO 2004/031141 A2 | 4/2004 |

OTHER PUBLICATIONS

International Search Report dated May 11, 2004 for PCT/US2003/026306.
International Search Report dated Jul. 2, 2004 for PCT/US2003/028548.
Supplementary European Search Report for EP 03798701.3 dated Jul. 19, 2006.

* cited by examiner

*Primary Examiner*—Karl Puttlitz
(74) *Attorney, Agent, or Firm*—Kilyk & Bowersox, P.L.L.C.

(57) ABSTRACT

A fluorocarboxylic acid preparation process which includes hydrolyzing fluorocarboxylic acid fluoride in the presence of an aqueous sulfuric acid solution to form a reaction product containing a fluorocarboxylic acid and hydrogen fluoride (present as hydrofluoric acid); and removing at least some of the hydrogen fluoride from the reaction product by washing the reaction production with aqueous sulfuric acid solution. The hydrolyzing and washing are carried out at a temperature at which the fluorocarboxylic acid is a liquid.

22 Claims, 1 Drawing Sheet

US 7,253,315 B2

PROCESS FOR PREPARING FLUOROCARBOXYLIC ACIDS

CROSS REFERENCE TO RELATED APPLICATIONS

The present application is a continuation of International Patent Application No. PCT/US2003/026306, filed Sep. 24, 2003, which in turn claims priority from U.S. Provisional Application No. 60/413,154 filed Sep. 25, 2002, incorporated herein by reference.

BACKGROUND OF THE INVENTION

1. Field of the Invention

The present invention relates to a process for preparing fluorocarboxylic acids and their derivatives. More particularly, it relates to a process for preparing fluorocarboxylic acids in high purity and in high yield from the corresponding fluorocarboxylic acid fluorides. The invention relates specifically to a process for preparing $C_{4-14}$, and especially $C_{7-9}$, fluorocarboxylic acids, including fluoroalkylcarboxylic acids, particularly perfluoroalkylcarboxylic acids, as well as derivatives thereof.

2. Description of the Related Art

Fluorocarboxylic acids, such as $C_8$ fluorocarboxylic acids and their derivatives, are known to have good surface activity. These fluorocarboxylic acids, as well as their ammonium salts and alkali metal salts, are widely used as polymerization emulsifying agents in the polymerization of fluoroolefins such as tetrafluoroethylene. Moreover, it is well known that such fluorocarboxylic acids are generally prepared by hydrolyzing the corresponding fluorocarboxylic acid fluorides.

In one known process for preparing perfluorocarboxylic acids, the reaction product of fuming sulfuric acid with a perfluoroalkyl iodide is subjected to liquid-liquid separation between a light liquid phase and a heavy liquid phase, the perfluorocarboxylic acid fluoride present in the separated light liquid phase is hydrolyzed to give a perfluorocarboxylic acid-containing reaction product, and the resulting reaction product is subjected to distillation and separation, yielding a perfluorocarboxylic acid (JP-B 2-61446, U.S. Pat. No. 4,400,325).

In this related art process, many impurities form because the separated light liquid phase is directly hydrolyzed without distillation. Moreover, owing to the hydrogen fluoride (and therefore hydrofluoric acid) which forms as a result of the hydrolysis reaction between perfluorocarboxylic acid fluoride and water, the distillation apparatus used for distillation following hydrolysis either must be made of a corrosion-resistant precious metal material, or must be lined with a material such as a fluorinated polymer (e.g., polytetrafluoroethylene) or copolymer.

Thus, a process in which a perfluorocarboxylic acid fluoride-containing light liquid phase is directly hydrolyzed does not lend itself readily to industrial application for reasons having to do with the materials of the process equipment. Moreover, the reaction product subjected to distillation following hydrolysis contains various reaction by-products as impurities. Removal of the impurities increases the complexity of perfluorocarboxylic acid purification. Furthermore, because perfluorocarboxylic acid has a high boiling point, distillation must be carried out under a vacuum. Hence, the conditions for removal of the impurities and distillation make the purification process complex.

Another related art process, proposed as a solution to the above-described problems, is a process for preparing high-purity perfluorocarboxylic acid fluoride by the preliminary distillation of a light liquid phase containing perfluorocarboxylic acid fluoride (JP-A 8-231462). In this process, high-purity perfluorocarboxylic acid fluoride obtained by distillation is added to water and subjected to a hydrolysis reaction, yielding perfluorocarboxylic acid. Hydrogen fluoride forms as a by-product at this time. By carrying out hydrolysis at a lower temperature than the melting point of perfluorocarboxylic acid, the above-described problem of handling hydrogen fluoride in a distillation step can be avoided as described below, thus making this an advantageous process with industrial potential.

For example, when a perfluorocarboxylic acid having eight or more carbon atoms is prepared, the perfluorocarboxylic acid obtained by hydrolysis is a solid substance at room temperature. Because water adheres to the surface of this solid substance, dehydration must be carried out. The melting point of a perfluorocarboxylic acid having eight carbon atoms, for instance, is 53° C. The dehydration operation is generally performed using a centrifugal dehydrator. The hydrogen fluoride present within the aqueous phase is removed at the same time. This method requires handling a solid, but solids are less easily handled than liquids. Moreover, the amount of perfluorocarboxylic acid which dissolves in the aqueous phase that is separated by centrifugation and its loss cannot be disregarded. Also, removal of the hydrogen fluoride present in the adhering water may require several washes, further increasing the loss of perfluorocarboxylic acid. Finally, cases that involve the handling of a solid substance do not lend themselves well to a continuous process.

One way to overcome the above problems relating to the separation of a hydrogen fluoride-containing aqueous phase from solid perfluorocarboxylic acid is a process in which the perfluorocarboxylic acid is melted in the presence of the aqueous phase and liquid separation is induced based on the poor solubility of perfluorocarboxylic acid in water, thereby separating the contents into an aqueous phase and a perfluorocarboxylic acid phase. In this method, under temperature conditions at or above the melting point of the perfluorocarboxylic acid, the perfluorocarboxylic acid is rendered into a molten state and can be obtained by separation into a hydrogen fluoride-containing aqueous phase and a perfluorocarboxylic acid-containing organic phase.

However, when preparing a perfluorocarboxylic acid having eight carbon atoms, for example, under temperature conditions at or above the melting point of perfluorocarboxylic acid, the perfluorocarboxylic acid and water form a gel over a wide range in composition, making liquid-liquid separation difficult. "Gel," as used herein, refers to a semisolid colloid having a three-dimensional network-like structure and lacking fluidity; that is, a physical gel. Hence, it is also not that easy to handle perfluorocarboxylic acid by melting it.

SUMMARY OF THE INVENTION

It is therefore an object of the present invention to resolve the above-described problems associated with prior-art processes for preparing fluorocarboxylic acid, particularly the problems associated with the purification process following hydrolysis, and thereby to provide a novel process for preparing fluorocarboxylic acids which process enables the industrial production of high-purity fluorocarboxylic acids in an economically beneficial manner. Moreover, because fluorocarboxylic acids generally are not biodegradable, to protect the environment, it is important to minimize the release of fluorocarboxylic acid outside the production process system. Accordingly, it is also an object of the invention to provide a process for preparing fluorocarboxylic acid by an effective method which reduces loss from the production system to a greater extent than the related art production processes described above.

We have found that the above objects can be achieved with a process for preparing fluorocarboxylic acids that includes the steps of hydrolyzing fluorocarboxylic acid fluoride in the presence of aqueous sulfuric acid solution to form a reaction product containing fluorocarboxylic acid and hydrogen fluoride (present as hydrofluoric acid); and removing at least some of the hydrofluoric acid from the reaction product by washing the reaction product with aqueous sulfuric acid solution.

BRIEF DESCRIPTION OF THE DRAWING

10: Karr tower
12: Cylindrical section
14: 16: Decanters
18: Plate
20: Shaft
22: Motor
23: Bottom end of cylindrical section
24: Reaction zone
26: Washing zone
28: interface
30: Top end of cylindrical section
32: Light liquid feed opening

DETAILED DESCRIPTION OF THE INVENTION

Figure 1:
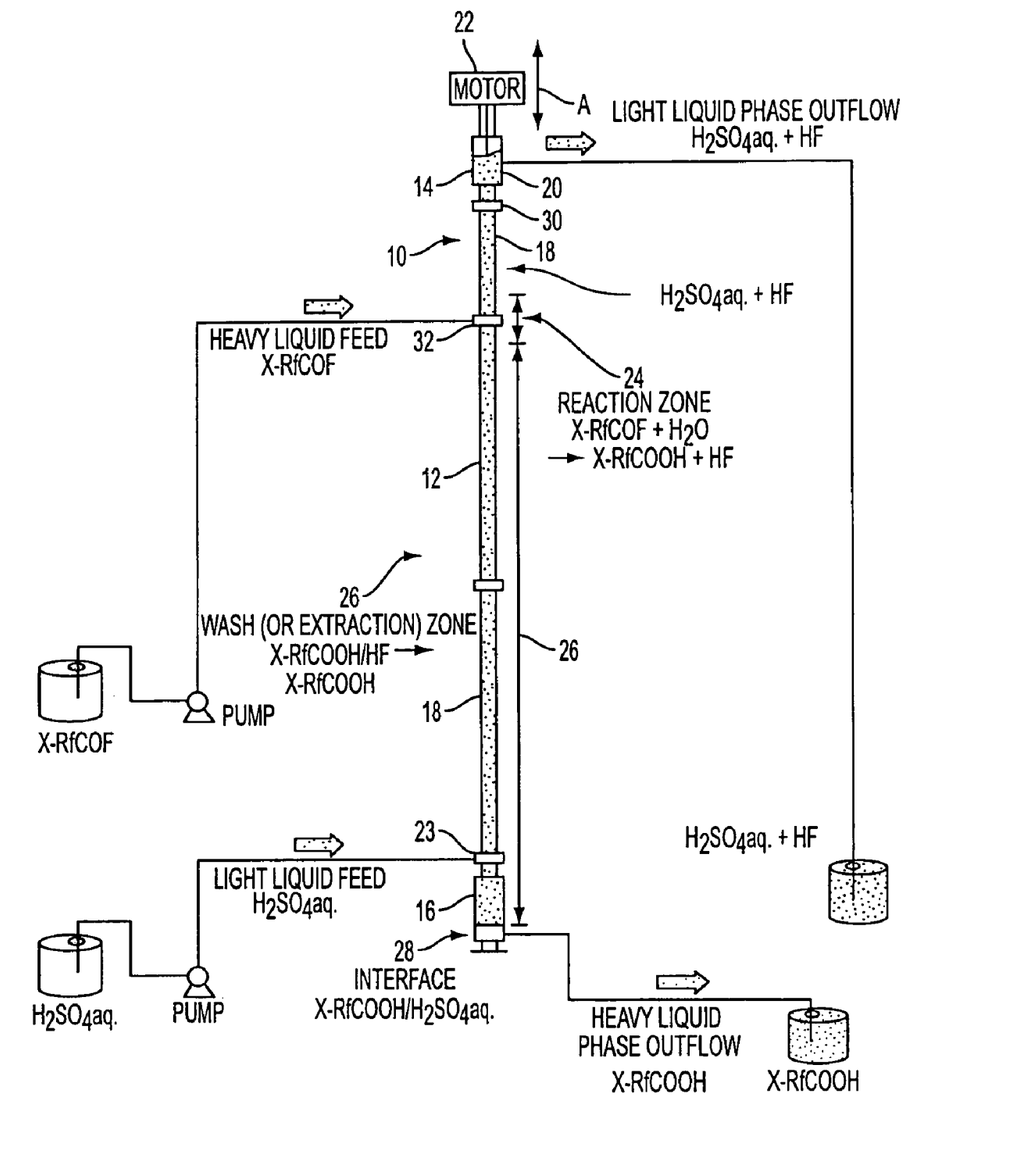
The FIGURE is a schematic flow sheet illustrating the fluorocarboxylic acid preparation process of the invention using a Karr tower. Reference symbols employed in the FIGURE are explained as follows.

In the preparation process of the invention, the fluorocarboxylic acid fluoride that is hydrolyzed is a compound having the general formula X—RfCOF          (1).

In the formula, X is a hydrogen atom, a fluorine atom or a chlorine atom. Rf is a linear or branched fluoroalkyl group of 4 to 14 carbons, and preferably 7 to 9 carbons, such as a linear or branched fluoroalkyl group of 8 carbons, and especially a linear or branched perfluoroalkyl group.

Therefore, the fluorocarboxylic acid prepared by hydrolysis has the general formula X—RfCOOH          (2).

In the formula, X and Rf are defined as above. Especially preferred examples of fluorocarboxylic acids that can be prepared by the inventive process include perfluoroalkylcarboxylic acids such as $C_7F_{15}COOH$ and $C_8F_{17}COOH$.

In the inventive process, the fluorocarboxylic acid fluoride and the fluorocarboxylic acid prepared therefrom mutually correspond. The term "correspond," as used in connection with these compounds, means that the group X—Rf remains unchanged before and after hydrolysis.

According to another embodiment of the invention, the fluorocarboxylic acid fluoride which is hydrolyzed is a compound having the general formula X—$(CF_2)_m$—O—$(CF(CF_3)CF_2O)_n$—$CF(CF_3)COF$          (3).

In the formula, X is a hydrogen atom, a fluorine atom or a chlorine atom; m is an integer from 1 to 10, such as 5; and n is an integer from 0 to 5, such as 0.

Therefore, the corresponding fluorocarboxylic acid prepared in this embodiment is a compound having the general formula X—$(CF_2)_m$—O—$(CF(CF_3)CF_2O)_n$—$CF(CF_3)COOH$          (4).

In the formula, X, m and n are defined as above.

In the inventive process, hydrolysis of fluorocarboxylic acid fluoride in the presence of aqueous sulfuric acid solution may be carried out under any suitable conditions and using any suitable apparatus, provided that the fluorocarboxylic acid fluoride and the fluorocarboxylic acid that forms are present in a liquid state. Generally, the reaction is carried out at a temperature higher than the melting point of the fluorocarboxylic acid which is formed, typically a temperature at least about 3° C. higher, and preferably a temperature at least about 5° C. higher, such as a temperature from about 5 to 15° C. higher. The hydrolysis reaction in the present invention, when carried out in the presence of excess water, can achieve a conversion (based on the fluorocarboxylic acid fluoride) close to substantially 100% in a relatively short reaction time. For example, in the preparation of linear $C_7F_{15}COOH$ (melting point, 53° C.), a conversion of substantially 100% is achieved when the hydrolysis reaction is carried out for a period of 2 to 5 minutes at 60 to 70° C.

The solubilities relating to the fluorocarboxylic acid prepared from the fluorocarboxylic acid fluoride, meaning the solubility of the fluorocarboxylic acid in the aqueous sulfuric acid solution and the solubility of sulfuric acid in the fluorocarboxylic acid, are both low. The hydrogen fluoride (water is present in the reaction system, so this is present as hydrofluoric acid) which forms concurrently with the fluorocarboxylic acid has low solubility in fluorocarboxylic acid, but high solubility in the aqueous sulfuric acid solution. Depending on the conditions, its solubility in the latter may even be unlimited.

As will be apparent from the foregoing discussion, in the inventive process, the hydrolysis reaction proceeds in a liquid (aqueous phase)-liquid (organic phase) heterophase dispersed (or mixed) system, at all stages, including the start of the reaction and at reaction completion.

(1) In the initial stage of the reaction, an aqueous phase containing sulfuric acid and an organic phase containing the carboxylic acid fluoride are present. The reaction begins and proceeds with mutual contact between these phases.

(2) In the intermediate stage of the reaction, an organic phase composed primarily of the fluorocarboxylic acid fluoride and the fluorocarboxylic acid that forms and a sulfuric acid-containing aqueous phase which contains the hydrogen fluoride that forms are both present.

(3) At the time of reaction completion, an organic phase composed primarily of fluorocarboxylic acid and an aqueous phase composed primarily of hydrogen fluoride and sulfuric acid are present.

In the inventive process, liquid separation between these phases is desirable. When the system is left at rest at any stage, whether before, during or after the hydrolysis reaction, an interface readily forms between the phases, and liquid separation occurs. The hydrogen fluoride formed by hydrolysis readily dissolves in the aqueous phase, but because some remains present in the organic phase, the washing operation described below is required to obtain high-purity fluorocarboxylic acid.

In the inventive process, a "reaction product" is obtained by hydrolysis. Here, "reaction product" is used to mean a mixture containing the compounds formed by the hydrolysis reaction. Therefore, the "reaction product" contains at least the compounds formed by the hydrolysis reaction (the fluorocarboxylic acid and the hydrogen fluoride). As noted above, in the inventive process, the hydrolysis reaction proceeds in a liquid-liquid heterophase dispersed system. In this type of reaction, it is not easy to separate only the compound formed by hydrolysis and subject it to the treatment described below.

Therefore, in addition to the fluorocarboxylic acid and hydrogen fluoride, the reaction product may include also other compounds (fluorocarboxylic acid fluoride, water, sulfuric acid, etc.) which are present when hydrolysis occurs, and generally does include such other compounds. The reaction product is preferably in the form of an organic phase (i.e., a phase composed primarily of fluorocarboxylic acid, within which sulfuric acid, water, hydrogen fluoride, fluorocarboxylic acid fluoride, etc., are dissolved), although it may also include an aqueous phase (i.e., a phase composed primarily of water and sulfuric acid, within which hydrogen fluoride, fluorocarboxylic acid, fluorocarboxylic acid fluoride, etc., are dissolved). The reaction product may be an organic phase alone, or a mixture of an organic phase and an aqueous phase. In the inventive process, this reaction product is washed in the manner described below.

In the process of the invention, the hydrolysis reaction can be started by, for example, dispersing liquid droplets of fluorocarboxylic acid fluoride as the dispersed phase in the aqueous sulfuric acid solution as the continuous phase. Hydrolysis is subsequently made to proceed by promoting contact and material transfer between the aqueous phase as the continuous phase and the organic phase as the dispersed phase. The dispersed phase and the continuous phase may be reversed. The hydrolysis reaction is carried out by mixing the organic phase and the aqueous phase for a given period of time. The reaction product resulting from hydrolysis can be obtained by halting mixture, subjecting the organic phase and the aqueous phase to liquid separation, and separating and collecting the organic phase. Alternatively, according to another embodiment, the reaction product may be obtained in the form of an organic phase containing some aqueous phase that arises as a result of incomplete liquid separation, or even as a mixture of the organic phase and the aqueous phase with no liquid separation whatsoever.

The reaction apparatus used for hydrolysis may generally be any suitable apparatus capable of mixing the organic phase and the aqueous phase, and carrying out a liquid-liquid heterophase dispersed system reaction. In an especially preferred embodiment, use is made of an apparatus capable of promoting the coalescence and re-dispersion of the dispersed phase in the continuous phase, such as a mixing tank. In another embodiment, a tubular reactor may be used. The tubular reactor may be a parallel current-type or countercurrent-type reactor. In the practice of the inventive process, at all stages of the reaction (including at the start and completion of the reaction), the organic phase generally has a greater specific gravity than the aqueous phase, and two phases—an organic phase and an aqueous phase—are generally present. Thus, when a tubular reactor is used, it is preferable for the reactor to be in the form of a tower-type reactor. In the inventive process, the hydrolysis reaction is a reaction between the organic phase and the aqueous phase. Given that mass transfer takes place across the boundary between the two phases, it is preferable to use as the reaction apparatus a differential contacting-type extraction apparatus, or "extraction tower." It is especially desirable for the extraction tower to be operated by means of countercurrent extraction.

The aqueous sulfuric acid solution has a sulfuric acid concentration during hydrolysis of about 5 to 50 wt %, preferably about 10 to 30 wt %, and most preferably about 15 to 20 wt %. The sulfuric aid concentration need not be constant throughout the reaction, provided the sulfuric acid concentration in the aqueous phase is maintained within the above-indicated concentration range from start to completion of the reaction. As used in the present specification, "sulfuric acid concentration" at the start of the reaction refers to the sulfuric acid concentration in the aqueous sulfuric acid solution used in the reaction, and after the start of the reaction refers to the concentration in the aqueous phase.

No particular limitation is imposed on the ratio between the respective amounts of the fluorocarboxylic acid fluoride and the aqueous sulfuric acid solution used in the reaction, provided water is present in at least the stoichiometric amount necessary for hydrolysis of the fluorocarboxylic acid fluoride that is present. The amount of water is generally greater, preferably at least about 1.2 times greater, and most preferably at least about 1.5 times greater, than the stoichiometric amount required for hydrolysis of the fluorocarboxylic acid fluoride fed to the reaction system. A greater amount of water is highly desirable because it increases the amount of the aqueous phase which takes up the hydrogen fluoride that forms. In this sense, water may be supplied to the reaction system in an amount that is, for example, about 5 to about 20 times, and especially about 10 to about 15 times, the stoichiometrically required amount of water.

In the inventive process, when hydrolysis is carried out batchwise, the above-mentioned sulfuric acid concentration is the sulfuric acid concentration in the aqueous sulfuric acid solution fed to the reaction system (e.g., mixing tank), and the weight ratio is the ratio of the sulfuric acid in the aqueous sulfuric acid solution fed to the reaction system with respect to the fluorocarboxylic acid fluoride. When hydrolysis is carried out continuously, the above-mentioned sulfuric acid concentration is the sulfuric acid concentration in the aqueous solution of sulfuric acid continuously fed to the reaction system (e.g., mixing tank, extraction tower), and the weight ratio is the ratio of the flow rate of water in the aqueous sulfuric acid solution fed to the reaction system with respect to the fluorocarboxylic acid fluoride.

The fluorocarboxylic acid fluoride which is hydrolyzed is not subject to any particular limitation, so long as the corresponding fluorocarboxylic acid can be obtained by working the inventive process. Preferred fluorocarboxylic acid fluorides include those having 4 to 14 carbons, and preferably 6 to 9 carbons, more preferably 7 or 8 carbons. Perfluoroalkylcarboxylic acid fluorides are especially preferred. The fluoroalkyl group may be a perfluoroalkyl group or a fluoroalkyl group in which at least one of the fluorines is substituted with hydrogen or chlorine. The fluoroalkyl group may be linear or branched.

The fluorocarboxylic acid fluoride may be prepared by any suitable process. The fluorocarboxylic acid fluoride may also include other components (e.g., fluoroalkyl iodide), insofar as these do not adversely affect the preparation process of the invention. More specifically, fluorocarboxylic acid fluoride obtained by the method described in JP-A 8-231462 may be used.

As noted above, hydrogen fluoride is readily taken up in the aqueous sulfuric acid solution, and thus in the aqueous phase. However, following hydrolysis, the entire amount of hydrogen fluoride is not immediately taken up; some of it remains in the organic phase. Accordingly, the reaction product obtained in the hydrolysis reaction, whether it is an organic phase only or in the form of a mixture of organic phase and aqueous phase, contains the hydrogen fluoride that forms in the reaction. Therefore, in the inventive process, by washing the reaction product with an aqueous sulfuric acid solution, at least part and preferably substantially all of the hydrogen fluoride (or hydrofluoric acid) within the organic phase is removed, thereby enhancing the purity of the fluorocarboxylic acid. In cases where the reaction product contains an aqueous phase as well, the aqueous phase is also removed by the aqueous sulfuric acid solution.

Such washing is an operation in which hydrogen fluoride present in the organic phase is extracted by the aqueous sulfuric acid solution. If the reaction product also contains some aqueous phase, the wash is an operation which allows the aqueous phase to coalesce with the aqueous sulfuric acid solution. As with the hydrolysis reaction, this mixture is carried out at a higher temperature than the melting point of the fluorocarboxylic acid, generally at a temperature at least about 3° C. higher, and preferably a temperature at least about 5° C. higher, such as a temperature about 5 to 15° C. higher. For example, in the preparation of linear $C_7F_{15}COOH$ (melting point, 53° C.), washing may be carried out at 60 to 70° C.

In the inventive process, as with the hydrolysis reaction, washing proceeds at all stages in a liquid (aqueous phase)-liquid (organic phase) heterophase dispersed system.

(1) At the initial stage of washing, an aqueous phase containing sulfuric acid and an organic phase containing fluorocarboxylic acid and hydrogen fluoride are present. These are mixed and brought into mutual contact, starting the wash in which the hydrogen fluoride transfers from the organic phase to the aqueous phase.

(2) At the completion of washing, an organic phase composed primarily of fluorocarboxylic acid and containing substantially no hydrogen fluoride, and an aqueous phase containing sulfuric acid and hydrogen fluoride are present.

In this type of wash, good separation occurs between these aqueous and organic phases. When the system is left at rest following mixture, an interface soon forms between the phases, and liquid separation occurs.

The aqueous sulfuric acid solution used for the wash has a sulfuric acid concentration of generally about 5 to 50 wt %, preferably about 10 to 30 wt %, and most preferably about 15 to 20 wt %. After washing has begun, the sulfuric acid concentration of the aqueous phase is important. The sulfuric acid concentration need not necessarily remain constant throughout the wash. As described above in connection with the aqueous sulfuric acid solution used in hydrolysis, the "sulfuric acid concentration" of the aqueous sulfuric acid solution used in washing is the same as the sulfuric acid concentration in the aqueous sulfuric acid solution fed at the start of washing, but differs from the concentration of the aqueous phase after washing has begun. So long as the sulfuric acid concentration in the aqueous phase is maintained within the above-indicated concentration range from the start to the completion of washing, gel formation can be effectively prevented.

Such washing is carried out with an aqueous sulfuric acid solution, but an aqueous sulfuric acid solution is used also in the hydrolysis reaction that precedes washing. Hence, the aqueous sulfuric acid solution used in hydrolysis may be the aqueous sulfuric acid solution that has been used in washing. Accordingly, the aqueous sulfuric acid solution used in hydrolysis may contain hydrogen fluoride. Moreover, the aqueous sulfuric acid solution used in hydrolysis may be used directly as is in washing, and so the aqueous sulfuric acid solution used in washing may contain hydrogen fluoride. The latter embodiment can be carried out by, after the reaction, taking up (i.e., extracting) the hydrogen fluoride that has formed into the aqueous sulfuric acid solution present in the reaction system, so that washing is in fact achieved by the transfer of hydrogen fluoride from the organic phase to the aqueous phase present around it at the time of the hydrolysis reaction.

The amount of aqueous sulfuric acid solution used in washing may be suitably selected according to the amount of reaction product to be washed, particularly the amount of organic phase (i.e., fluorocarboxylic acid phase) therein, and most particularly the amount of hydrogen fluoride present therein. Washing is carried out at a weight ratio of the amount of aqueous sulfuric acid solution used (S) to the amount of reaction product to be washed (F), or S/F, in a range of generally about 1 to 10, preferably about 1 to 5, and most preferably about 1 to 2. This ratio S/F is based on the amounts S and F fed to the washing operation, although it is preferable for the above range to be maintained during washing as well.

As will be described subsequently, washing may be carried out either in a batchwise manner or continuously. The ratio S/F is a weight ratio of the aqueous sulfuric acid solution fed to the washing system (e.g., a washing tank) to the reaction product, and preferably the organic phase therein. In cases where washing is carried out continuously, S/F is the weight ratio of the flow rate of aqueous sulfuric acid solution fed continuously to the washing system (e.g., mixing tank, washing tower) to the flow rate of the reaction mixture, and preferably of the organic phase therein. In the method of the invention, the fluorocarboxylic acid fluoride is converted to the corresponding fluorocarboxylic acid, although the number of moles thereof do not change through reaction and washing. Accordingly, because the amount of organic phase does not undergo a large change throughout the reaction and washing, in an industrial operation, F may approximately be regarded as identical to the amount of fluorocarboxylic acid fluoride fed to the reaction.

Washing is carried out by mixing the reaction mixture and the aqueous sulfuric acid solution, placing the system at rest to allow liquid separation into two phases to occur—an organic phase composed primarily of fluorocarboxylic acid and an aqueous phase composed primarily of sulfuric acid and water, then separating and collecting the organic phase. Under the liquid separation conditions, the organic phase and the aqueous phase are in equilibrium. Therefore, the organic phase contains amounts of water, sulfuric acid and hydrogen fluoride corresponding to their saturation solubilities under the liquid-liquid separation conditions, but these amounts are all small. The amount of hydrogen fluoride in particular is very low. If necessary, the amount of hydrogen fluoride can be reduced by subjecting the organic phase that has been collected to another wash with aqueous sulfuric acid solution. Accordingly, in the inventive process, it is possible by means of washing to obtain fluorocarboxylic acid in which the hydrogen fluoride concentration has been reduced, and preferably from which the hydrogen fluoride has been substantially removed. Depending on the intended use of the fluorocarboxylic acid obtained after washing, additional treatment to remove hydrogen fluoride may be omitted. As in the case of the hydrolysis reaction, when the system is placed at rest following mixture during the washing operation, separation of the fluorocarboxylic acid phase and the aqueous sulfuric acid solution phase is good. Moreover, the amount of fluorocarboxylic acid present in the aqueous phase is low.

For example when $C_7F_{15}COOH$ and a 15 wt % aqueous sulfuric acid solution are mixed in a 1:1 weight ratio, then the layers allowed to separate, the sulfuric acid present in the organic $C_7F_{15}COOH$ phase is only about 3,000 ppm by weight (amount in the $C_7F_{15}COOH$ solid). At this sulfuric acid concentration, depending on the intended use of the $C_7F_{15}COOH$, additional purification steps can often be omitted. The $C_7F_{15}COOH$ concentration in the aqueous sulfuric acid solution phase (aqueous phase) is less than 100 ppm by weight. This means that the loss of fluorocarboxylic acid present in the aqueous phase discarded as process waste water can be minimized.

In the process for preparing fluorocarboxylic acid according to the invention, washing can be carried out continuously or in a batchwise manner. In cases where it is carried out in a batchwise fashion, the reaction mixture obtained by the hydrolysis reaction and the aqueous sulfuric acid solution are thoroughly mixed, following which the liquid mixture is placed at rest to allow the organic phase containing the target fluorocarboxylic acid and the aqueous phase containing hydrogen fluoride and sulfuric acid to separate, and the organic phase is separated off and collected. If necessary, the resulting organic phase may be mixed with fresh (that is, free of hydrogen fluoride) aqueous sulfuric acid solution, and the mixture placed at rest to obtain an organic phase having an even lower amount of hydrogen fluoride. Washing can be repeated in this way until the concentration of hydrogen fluoride in the aqueous phase falls below the desired level. Such a batch-type washing operation can be carried out by placing the aqueous sulfuric acid solution and the reaction mixture in a mixing tank, agitating the contents for a given length of time, then halting agitation so as to allow liquid separation to occur.

The washing operation is a type of extraction operation. Accordingly, instead of batchwise washing as described above, washing can be carried out in the same way as a continuous extraction operation. In an especially preferred embodiment, washing can be continuously carried out by countercurrent contacting aqueous sulfuric acid solution with the reaction product formed by the reaction. More specifically, washing may be carried out using an extraction column by feeding the aqueous sulfuric acid solution as the light, i.e. lower density, liquid and the reaction mixture as the heavy, i.e. higher density, liquid, and inducing countercurrent contact between the two liquids. The operation may be carried out with the aqueous phase serving as the continuous phase, and the organic phase serving as the dispersed phase, or vice versa.

In the inventive process, an aqueous sulfuric acid solution is used in both the reaction and washing. However, because sulfuric acid is not consumed in the hydrolysis reaction and washing, the amount of sulfuric acid theoretically does not increase or decrease. Accordingly, as will be apparent from the preceding discussion, in the present invention the sulfuric acid concentration of the aqueous phase during washing is substantially the same as or little changed from the sulfuric acid concentration of the aqueous phase during the reaction. That is, the aqueous sulfuric acid solution used in the hydrolysis reaction may be used in washing (actually, some of the hydrogen fluoride formed by the hydrolysis reaction is extracted by the aqueous sulfuric acid solution present in the reaction system, and can thus be said to have been washed out). Conversely, aqueous sulfuric acid solution used in washing can be used in the hydrolysis reaction.

In one embodiment, the sulfuric acid concentration of the aqueous sulfuric acid solution used in washing may be the same as the sulfuric acid concentration of the aqueous sulfuric acid solution used in the hydrolysis reaction described above. Accordingly, in the inventive process, the hydrolysis of fluorocarboxylic acid fluoride is carried out in the presence of an aqueous phase that has already been used in washing. This is especially advantageous when these steps are carried out continuously.

Specifically, (a) a sulfuric acid-containing aqueous phase and a fluorocarboxylic acid-containing organic phase are obtained by liquid-liquid separation following washing, and the aqueous phase is utilized in hydrolysis; (b) next, the aqueous phase and the fluorocarboxylic acid fluoride are mixed and subjected to hydrolysis, following which the system is placed at rest, giving a fluorocarboxylic acid-containing organic layer and an aqueous layer; (c) this organic layer is washed with the aqueous sulfuric acid solution, and the aqueous phase formed by such washing is used in hydrolysis. Step (c) is the same as above step (a). By repeating steps (a) to (c), the inventive process can be carried out continuously. Indeed, carrying out the inventive process in this way is preferred. In this type of continuous operation, a reaction apparatus (the apparatus of step (b)) which carries out hydrolysis and a washing apparatus (the apparatus of step (a)) which carries out washing are each provided, the reaction product that arises from hydrolysis may be continuously fed from the reaction apparatus to the washing apparatus, and the aqueous phase that arises from washing may be continuously fed from the washing apparatus to the reaction apparatus. However, in cases where the inventive process is carried out on an industrial scale, it is preferable to carry out reaction and washing continuously using a single apparatus.

It is especially preferable to use, as such a single apparatus, a countercurrent differential extraction tower capable of continuously countercurrent-contacting the light liquid phase and the heavy liquid phase. Various extraction apparatuses capable of countercurrent operation are known. Specific examples of such apparatuses that may be used include agitated plate-type extraction towers (e.g., rotary-disk extraction towers) and non-agitated plate-type extraction towers (e.g., perforated-plate extraction towers). Using such equipment, hydrolysis and washing can be continuously carried out by countercurrent contact between the organic phase and the aqueous phase.

An especially preferred type of extraction apparatus for carrying out the inventive process are the extraction towers sold by Sumitomo Heavy Industries Ltd. as Karr towers. Karr towers have a cylindrical section, and have receptacles that function as decanters and are positioned above and below the cylindrical section.

When the inventive process is carried out using this type of extraction tower, the aqueous sulfuric acid solution is continuously fed as the light liquid from the bottom of the cylindrical section and, as the aqueous phase, forms a continuous phase which rises up through the tower. The fluorocarboxylic acid fluoride is continuously fed as the heavy liquid from the top of the cylindrical section and, as the organic phase, becomes the dispersed phase which descends through the tower (actually, the fluorocarboxylic acid fluoride present in the descending dispersed phase is hydrolyzed to fluorocarboxylic acid). The hydrolysis reaction proceeds continuously through countercurrent contact during the period that the fluorocarboxylic acid fluoride is fed to the interior of the extraction tower and descends while contacting the aqueous sulfuric acid solution-containing aqueous phase rising up through the tower, as a result of which the fluorocarboxylic acid fluoride serving as the heavy liquid is converted to fluorocarboxylic acid. The organic phase may be the continuous phase, and the aqueous phase may be the dispersed phase. Hydrolysis begins in the vicinity of the fluorocarboxylic acid fluoride feed opening to the extraction tower.

Some of the hydrogen fluoride (which becomes hydrofluoric acid because water is present) formed by the hydrolysis reaction is present in the sulfuric acid-containing aqueous phase, and the remainder is present in the fluorocarboxylic acid-containing organic phase. During the period that the organic phase descends up through the tower in the form of liquid droplets as the dispersed phase, it comes into countercurrent contact with the aqueous sulfuric acid solution continuous phase ascending through the tower. Such contact causes the transfer, or extraction, of hydrogen fluoride present within the organic phase into the aqueous phase, thereby washing the organic phase.

This hydrolysis of the fluorocarboxylic acid fluoride and washing of the organic phase which contains the fluorocarboxylic acid formed as a result of the reaction are influenced by various equipment parameters that affect the extraction performance (e.g., length of the cylindrical section) and various operation parameters (e.g., flow rate of the fluorocarboxylic acid fluoride being fed, and the concentration and flow rate of the aqueous sulfuric acid solution being fed). Generally, hydrolysis of the fluorocarboxylic acid fluoride can achieve substantially 100% conversion in the presence of sufficient water and sufficient contact time. Removal (extraction efficiency) of the hydrogen fluoride from the resulting reaction mixture can be controlled by adjusting the above parameters. Those skilled in the art will be capable of carrying out the desired hydrolysis and washing by setting the equipment and operation parameters to suitable values.

When the extraction tower is operated as described above, the organic phase in the form of liquid droplets which contains the fluorocarboxylic acid following extraction of hydrogen fluoride by the aqueous sulfuric acid solution accumulates and coalesces at the bottom of the cylindrical section or in the bottom receptacle, forming a single organic phase. Continuous removal of this organic phase enables the fluorocarboxylic acid preparation process to be made continuous. The recovered organic phase, i.e., the fluorocarboxylic acid phase, has a small amount of impurities (e.g., water, sulfuric acid, fluorocarboxylic acid fluoride). This amount is a level which, depending on the intended use of the fluorocarboxylic acid, enables the simplification, and preferably the reduction, of subsequent purification treatment. Accordingly, the present invention provides a process for the continuous preparation of fluorocarboxylic acid, which process includes continuous hydrolysis treatment of fluorocarboxylic acid fluoride and continuous washing treatment of the resulting reaction product. More specifically, the invention provides a process for the preparation of fluorocarboxylic acid, which process includes hydrolysis by countercurrent contacting a fluorocarboxylic acid fluoride-containing organic phase with a sulfuric acid-containing aqueous phase, and washing by countercurrent contacting an organic phase containing hydrogen fluoride and fluorocarboxylic acid with a sulfuric acid-containing aqueous phase.

The present invention encompasses also methods in which a fluorocarboxylic acid prepared by the above-described process, such as a perfluorocarboxylic acid, is reacted with ammonia, for example, to form a fluorocarboxylic acid ammonium salt. That is, the invention provides a method of preparing fluorocarboxylic acid derivatives, which method is characterized by using an alkali to convert a fluorocarboxylic acid obtained by the above-described process into a salt.

As noted above, the inventive process for preparing fluorocarboxylic acid can be continuously carried out by using preferably a Karr extraction tower. A Karr extraction tower has numerous disk-like plates arranged within the cylindrical section of the extraction tower. These plates can be moved vertically within the cylindrical section. By means of such vertical movement, the continuous phase and the dispersed phase are efficiently contacted within the cylindrical section, and the dispersed phase is efficiently coalesced and redispersed. Parameters that exert an influence on extraction by such an apparatus include, in addition to ordinary extraction apparatus parameters, include the size of the vertically moving plates, the interval between neighboring plates, and the frequency of vertical movement. Suitable hydrolysis and washing can be carried out by adjusting these parameters.

The FIGURE shows a flow sheet illustrating how the inventive process is carried out using this type of Karr tower 10. The Karr tower 10 is composed of a cylindrical section 12 and receptacles 14 and 16 positioned at the top and bottom ends thereof. A plurality of disk-like plates 18 are arranged inside the cylindrical section. These are mounted on a shaft 20 at the center axis of the tower. The shaft moves vertically in the manner indicated by the arrows A under the prompting of a motor 22 provided at the top of the tower. The vertical movement by this shaft 20 causes the plates 18 to move up and down.

For example, a 15 wt % aqueous sulfuric acid solution ($H_2SO_4$ aq.) is supplied as the light liquid feed from the bottom 23 of the cylindrical section 12 to the tower 10, and liquid fluorocarboxylic acid fluoride (X—RfCOF) is supplied as the heavy liquid feed to an upper portion 32 of the cylindrical section of the Karr tower by a pump (the heavy liquid need not be fed in at the top end; as shown in the diagram, it may be fed in at a point somewhat downward from the top end). To ensure that hydrolysis and washing are carried out at a temperature higher than the melting point of the fluorocarboxylic acid, the temperature of the liquids that are fed to the tower and the temperature of the liquids inside the tower are controlled. In the illustrated embodiment, the aqueous sulfuric acid solution rises through the tower and forms an aqueous phase serving as the continuous phase. The fluorocarboxylic acid fluoride descends through the tower, and forms an organic phase as the dispersed phase.

Upon entering the tower, the fluorocarboxylic acid fluoride that has been fed to the tower is hydrolyzed in the presence of the sulfuric acid and water present therein (i.e., in the presence of an aqueous sulfuric acid solution), forming fluorocarboxylic acid (X—RfCOOH) and hydrogen fluoride. This hydrolysis reaction occurs in the vicinity of the fluorocarboxylic acid fluoride feed opening 32 to the tower. Hence, the vicinity of the fluorocarboxylic acid fluoride feed opening in the tower (the areas above and below) become the hydrolysis reaction zone 24 where the reaction shown in the FIGURE occurs. As is apparent from the description given above, the fluorocarboxylic acid fluoride present in the organic phase is converted to fluorocarboxylic acid in the reaction zone 24, following which it descends in the state of liquid droplets through a washing zone 26 located below the reaction zone 24. During this descent, the hydrogen fluoride present in the organic phase transfers (i.e., is extracted) into the aqueous phase, as a result of which the organic phase is washed.

The organic phase that descends through the tower accumulates in the receptacle 16 and the liquid droplets coalesce, forming a single organic phase, resulting in the formation of an interface 28 with the aqueous phase. The organic phase is composed primarily of fluorocarboxylic acid, and contains only a very small amount of hydrogen fluoride. This organic phase is removed as heavy liquid phase outflow, affording fluorocarboxylic acid containing substantially no hydrogen fluoride. This fluorocarboxylic acid contains water and sulfuric acid dissolved therein. The sulfuric acid and/or water may be removed, depending on the intended use of the fluorocarboxylic acid. Removal of the water and sulfuric acid may be achieved, for example, by distillation treatment.

The aqueous sulfuric acid solution which rises through the tower washes the descending organic phase in the washing zone 26, becoming a hydrogen fluoride-containing aqueous phase. It then enters the reaction zone 24, where it provides a place for hydrolysis of the fluorocarboxylic acid fluoride, takes up some of the hydrogen fluoride formed by hydrolysis, then leaves the reaction zone and reaches receptacle 14. It then overflows from receptacle 14 as light liquid phase outflow, and is discharged from the tower.

EXAMPLES

Examples of the invention and comparative examples are described below. The present invention should not be construed as being limited thereto.

Example 1

Batchwise Reaction/Washing

A 250 ml perfluoroalkoxy resin (PFA) vessel equipped with a stirrer was used. A 15 wt % aqueous sulfuric acid solution (100 g) was temperature conditioned to 60° C. within the vessel, following which $C_7F_{15}COF$ (50 g, 0.120 mol; prepared by the method described in JP-A 8-231462) having a purity of 99.9 wt % was added dropwise over a period of two minutes to the aqueous sulfuric acid solution under stirring. Stirring was carried out thereafter for 15 minutes, after which the mixture is allowed to stand for 15 minutes, resulting in liquid separation into a top phase and a bottom phase. The bottom phase was an organic phase containing $C_7F_{15}COOH$, and the top phase was an aqueous phase containing water and sulfuric acid. This mixture exhibited good liquid-liquid separation.

The bottom phase was separated off and recovered, following which its composition was determined. The following results were obtained.

| | |
|---|---|
| $C_7F_{15}COOH$ | 93 wt % |
| $H_2O$ | 6.5 wt % |
| $H_2SO_4$ | 3,290 ppm by weight |
| HF | 1,370 ppm by weight |

The top phase had a $C_7F_{15}COOH$ concentration of 8 ppm by weight.

Next, using a 500 ml PFA vessel equipped with a stirrer, 15 wt % of an aqueous sulfuric acid solution (100 g) temperature conditioned to 60° C. was added under stirring to the recovered bottom phase, and the hydrogen fluoride was removed by washing. After 15 minutes of stirring, the mixture was allowed to stand for 15 minutes, resulting in liquid separation. This mixture exhibited good liquid-liquid separation. The bottom phase was an organic phase containing $C_7F_{15}COOH$, and the top phase was an aqueous phase containing water and sulfuric acid (i.e., an aqueous sulfuric acid solution ($H_2SO_4$ aq. phase). The recovered bottom phase (i.e., $C_7F_{15}COOH$ phase) was washed again in the same way.

The bottom phase was separated and recovered, following which its composition was determined. The following results were obtained.

| | |
|---|---|
| $C_7F_{15}COOH$ | 94 wt % |
| $H_2O$ | 5.6 wt % |
| $H_2SO_4$ | 4,180 ppm by weight |
| HF | 5 ppm by weight |

The top phase had a $C_7F_{15}COOH$ concentration of 15 ppm by weight.

Examples 2 to 5

Aside from varying the sulfuric acid concentration of the aqueous sulfuric acid solution used in hydrolysis and washing, the procedure followed in each of these examples was the same as that in Example 1. The top and bottom phases obtained after hydrolysis and after the two washes were analyzed. The results are given in Table 1 below.

Example 6

Aside from changing the temperature of the aqueous sulfuric acid solution used in hydrolysis and washing to 80° C., the same procedure was followed as in Example 1. The top and bottom phases obtained after hydrolysis and after the two washes were analyzed. The results are given in Table 1 below.

TABLE 1

Measured compositions of top and bottom phases after hydrolysis and after washing.

| | Top phase ($H_2SO_4$ aq. phase) | | Bottom phase ($C_7F_{15}COOH$ phase) | | | | | |
|---|---|---|---|---|---|---|---|---|
| | $C_7F_{15}COOH$ concentration (ppm by weight) | | $C_7F_{15}COOH$ concentration (wt %) | | HF concentration (ppm by weight) | | $H_2SO_4$ concentration (ppm by weight) | |
| Examples ($H_2SO_4$ concentration, wt %) | after hydrolysis | after washing | after hydrolysis | after washing | after hydrolysis | after washing | after hydrolysis | after washing |
| 2 (5) | 2,360 | 3,220 | 58 | 38 | 7,630 | 486 | 42,500 | 44,000 |

TABLE 1-continued

Measured compositions of top and bottom phases after hydrolysis and after washing.

| Examples ($H_2SO_4$ concentration, wt %) | Top phase ($H_2SO_4$ aq. phase) | | Bottom phase ($C_7F_{15}COOH$ phase) | | | | | |
|---|---|---|---|---|---|---|---|---|
| | $C_7F_{15}COOH$ concentration (ppm by weight) | | $C_7F_{15}COOH$ concentration (wt %) | | HF concentration (ppm by weight) | | $H_2SO_4$ concentration (ppm by weight) | |
| | after hydrolysis | after washing | after hydrolysis | after washing | after hydrolysis | after washing | after hydrolysis | after washing |
| 3 (10) | 10 | 26 | 89 | 80 | 2,600 | 71 | 13,000 | 13,500 |
| 4 (20) | 13 | 26 | 93 | 95 | 1,250 | 9 | 3,500 | 3,600 |
| 5 (30) | 183 | 494 | 93 | 95 | 1,280 | 17 | 4,190 | 4,270 |
| 6 (15) | 21 | 25 | 89 | 88 | 1,690 | 24 | 2,470 | 2,950 |

Comparative Example 1

A 250 ml PFA vessel equipped with a stirrer was used. Water (100 g, 5.6 mol) was temperature conditioned to 60° C. within the vessel, following which $C_7F_{15}COF$ (50 g, 0.120 mol; prepared by the method described in JP-A 8-231462) having a purity of 99.9 wt % was added dropwise under stirring in an attempt to form $C_7F_{15}COOH$ by a hydrolysis reaction. However, a gel formed, which made stirring impossible.

Comparative Example 2

A 250 ml PFA vessel equipped with a stirrer was used. Water (100 g, 5.6 mol) was temperature conditioned to 60° C. within the vessel, following which $C_7F_{15}COF$ (50 g, solid; prepared by the method described in JP-A 8-231462) having a purity of 99.9 wt % was added to the water under stirring. The solid $C_7F_{15}COOH$ gradually dissolved. However, the mixture became increasingly viscous, ultimately forming a gel, which made stirring impossible.

Aside from charging the water and $C_7F_{15}COOH$ in different proportions or changing the mixing temperature, the same experiment was repeated in the same way as described. The results are given below in Table 2.

TABLE 2

$C_7F_{15}COOH$ and water mixing conditions, and the state of the mixture.

| | Amount charged | | Temperature and state of mixture | | |
|---|---|---|---|---|---|
| Example No. | $C_7F_{15}COOH$ (g) | $H_2O$ (g) | 60° C. | 80° C. | 95° C. |
| 1 | 95 | 5 | liquid | liquid | liquid |
| 2 | 90 | 10 | liquid | liquid | liquid |
| 3 | 80 | 20 | gel | liquid | liquid |
| 4 | 70 | 30 | gel | gel | liquid |
| 5 | 60 | 40 | gel | gel | liquid |
| 6 | 50 | 50 | gel | gel | liquid |
| 7 | 40 | 60 | gel | gel | gel |
| 8 | 30 | 70 | gel | gel | gel |
| 9 | 20 | 80 | liquid | gel | gel |
| 10 | 10 | 90 | liquid | liquid | gel |
| 11 | 5 | 95 | liquid | liquid | gel |

Example 7

Continuous Hydrolysis/Washing

The Karr extraction tower shown in the FIGURE was used in this example. This tower had a cylindrical section 12 (length, 3.0 m) of 2.5 cm diameter, above and below which were positioned receptacles 14 and 16 as decanters. At the interior of the cylindrical section, disk-like plates 18 (55 plates positioned at 5 cm intervals) were moved vertically so as to agitate the liquid within the cylindrical section.

An aqueous sulfuric acid solution (15 wt %) was continuously fed as the light liquid at a flow rate of 200 g/min from the vicinity of the bottom end 23 of the cylindrical section. A 99.9 wt % pure $C_7F_{15}COF$ (prepared by the method described in JP-A 8-231462) was continuously fed as the heavy liquid at a flow rate of 50 g/min from a feed opening 32 provided at a position 0.6 m from the top end 30 of the cylindrical section, thereby forming a dispersed phase. In this example, operation was carried out using the aqueous sulfuric acid solution as the continuous phase and using $C_7F_{15}COF$ as the dispersed phase.

The $C_7F_{15}COF$ hydrolysis reaction arises continuously in the vicinity (reaction zone 24) of where $C_7F_{15}COF$ is fed to the aqueous sulfuric acid solution serving as the continuous phase. As the $C_7F_{15}COF$ serving as the dispersed phase and the heavy liquid is being converted by the hydrolysis reaction to $C_7F_{15}COOH$, it descends in the form of liquid droplets within the aqueous sulfuric acid solution as a $C_7F_{15}COOH$ phase.

Hydrogen fluoride formed by the hydrolysis reaction is present in the $C_7F_{15}COOH$ phase, but during descent through the tower, it is continuously extracted (i.e., washed) at the washing zone 26 by the aqueous sulfuric acid solution rising up through the tower. The descending $C_7F_{15}COOH$ dispersed phase coalesces in the decanter 16 at the bottom of the tower and liquid separation occurs, resulting in the formation of an interface 28 with the aqueous sulfuric acid solution.

The $C_7F_{15}COOH$ phase that formed in the decanter 16 at the bottom of the tower was recovered, and its composition was determined. The following results were obtained.

| $C_7F_{15}COOH$ | 94.2 wt % |
|---|---|
| $H_2O$ | 5.5 wt % |
| $H_2SO_4$ | 2,500 ppm by weight |
| HF | 2 ppm by weight |

No $C_7F_{15}COF$ was detected.

The continuous phase (i.e., aqueous sulfuric acid solution phase) in the decanter 14 at the top of the tower was collected, and the $C_7F_{15}COOH$ concentration therein was analyzed. The concentration was 50 ppm by weight. Assuming that all of the $C_7F_{15}COF$ supplied was hydrolyzed in the above-described hydrolysis and washing operations, the percent recovery of $C_7F_{15}COOH$ was 99.9%.

Comparative Example 3

Removal of HF from $C_7F_{15}COOH$ by Solid-Liquid Separation

A 500 ml PFA vessel equipped with a stirrer was used. Water (250 g, 13.9 mol) was temperature conditioned to 15° C. within the vessel, following which $C_7F_{15}COF$ (125 g, 0.3 mol) having a purity of 99.9 wt % was added dropwise under stirring. The resulting mixture was a solid-liquid dispersed system composed of an aqueous phase containing the hydrogen fluoride that formed in hydrolysis, and a solid phase of the $C_7F_{15}COOH$ that formed in hydrolysis.

The mixture was cooled to 5° C. under stirring, and solid-liquid separation was carried out with a centrifugal dehydrator. The recovered $C_7F_{15}COOH$ (127 g) contained 2.0 wt % of water and 1,200 ppm by weight of hydrogen fluoride. The wastewater from the centrifugal dehydrator had a $C_7F_{15}COOH$ concentration of 450 ppm by weight, and a hydrogen fluoride concentration of 2.3 wt %.

In a 500 ml PFA vessel equipped with a stirrer and using water (250 ml) temperature conditioned to 5° C., the $C_7F_{15}COOH$ recovered by centrifugal separation was stirred and washed so as to extract the hydrogen fluoride into the water. This was followed by solid-liquid separation with a centrifugal separator in the same way as described above.

The $C_7F_{15}COOH$ (123 g) recovered from the centrifugal dehydrator contained 2.0 wt % of water and 5 ppm by weight of hydrogen fluoride. The centrifugal dehydrator wastewater had a $C_7F_{15}COOH$ concentration of 2,500 ppm by weight and a hydrogen fluoride concentration of 570 ppm by weight. The percent recovery of $C_7F_{15}COOH$ following the above hydrolysis and washing was 99.4%.

It should further be apparent to those skilled in the art that various changes in form and detail of the invention as shown and described may be made. It is intended that such changes be included within the spirit and scope of the claims appended hereto.

What is claimed is:

1. A process for preparing fluorocarboxylic acid, which comprises:
    hydrolyzing a fluorocarboxylic acid fluoride in the presence of an aqueous sulfuric acid solution to form a reaction product containing a fluorocarboxylic acid and hydrogen fluoride; and
    removing at least some of the hydrogen fluoride from the reaction product by washing the reaction product with an aqueous sulfuric acid solution,
    wherein said hydrolyzing and said washing are carried out at a temperature at which said fluorocarboxylic acid is a liquid.

2. The process of claim 1, wherein the fluorocarboxylic acid fluoride has the general formula X—RfCOF in which X is a hydrogen atom, a fluorine atom or a chlorine atom, and Rf is a linear or branched fluoroalkyl group of 4 to 14 carbons.

3. The process of claim 2, wherein the fluorocarboxylic acid fluoride has the general formula X—$(CF_2)_m$—O—$(CF(CF_3)CF_2O)_n$—$CF(CF_3)COF$ in which X is a hydrogen atom, a fluorine atom or a chlorine atom, m is an integer from 1 to 10, and n is an integer from 0 to 5.

4. The process of claim 1, which comprises hydrolyzing said fluorocarboxylic acid fluoride in a liquid-liquid heterophase dispersed system including an aqueous phase and an organic phase, and maintaining the aqueous phase at a sulfuric acid concentration of about 5 to 50 wt %.

5. The process of claim 1, which comprises washing the reaction product with a liquid-liquid heterophase dispersed system including an aqueous phase and an organic phase, and maintaining the aqueous phase at a sulfuric acid concentration of about 5 to 50 wt %.

6. The process of claim 4, wherein hydrolysis is carried out continuously by countercurrent contact between the organic phase and the aqueous phase.

7. The process of claim 5, wherein washing is carried out continuously by countercurrent contact between the organic phase and the aqueous phase.

8. The process of claim 1, which comprises hydrolyzing said fluorocarboxylic acid fluoride and washing the reaction product both in a liquid-liquid heterophase dispersed system including an aqueous phase and an organic phase, and maintaining the aqueous phase at a sulfuric acid concentration of about 5 to 50 wt %, wherein hydrolysis and washing are carried out continuously by countercurrent contact between the organic phase and the aqueous phase in a single apparatus.

9. The process of claim 8, wherein said apparatus comprises a differential contacting extraction tower.

10. The process of claim 1, wherein the fluorocarboxylic acid fluoride comprises $C_7F_{15}COF$.

11. The process of claim 1, wherein said hydrolysis and washing are carried out batchwise.

12. A process for purifying a reaction product containing a fluorocarboxylic acid and hydrogen fluoride as a by-product, which comprises:
    washing the reaction product with an aqueous sulfuric acid solution to remove at least some of the hydrogen fluoride.

13. The process of claim 12, which comprises washing the reaction product with a liquid-liquid heterophase dispersed system including an aqueous phase and an organic phase, and maintaining the aqueous phase at a sulfuric acid concentration of about 5 to 50 wt %.

14. The process of claim 13, wherein washing is carried out continuously by countercurrent contact between the organic phase and the aqueous phase.

15. The process of claim 12, wherein said washing is carried out batchwise.

16. A process for preparing fluorocarboxylic acid, which comprises:
    hydrolyzing a fluorocarboxylic acid fluoride in the presence of an aqueous sulfuric acid solution to form a reaction product containing a fluorocarboxylic acid and hydrogen fluoride.

17. The process of claim 16, wherein the fluorocarboxylic acid fluoride has the general formula X—RfCOF in which X is a hydrogen atom, a fluorine atom or a chlorine atom, and Rf is a linear or branched fluoroalkyl group of 4 to 14 carbons.

18. The process of claim 17, wherein the fluorocarboxylic acid fluoride has the general formula $$X-(CF_2)_m-O-(CF(CF_3)CF_2O)_n-CF(CF_3)COF$$

in which X is a hydrogen atom, a fluorine atom or a chlorine atom, m is an integer from 1 to 10, and n is an integer from 0 to 5.

19. The process of claim 16, which comprises hydrolyzing said fluorocarboxylic acid fluoride in a liquid-liquid heterophase dispersed system including an aqueous phase and an organic phase, and maintaining the aqueous phase at a sulfuric acid concentration of about 5 to 50 wt %.

20. The process of claim 19, wherein hydrolysis is carried out continuously by countercurrent contact between the organic phase and the aqueous phase.

21. The process of claim 16, wherein the fluorocarboxylic acid fluoride comprises $C_7F_{15}COF$.

22. The process of claim 16, wherein said hydrolysis is carried out batchwise.

* * * * *

UNITED STATES PATENT AND TRADEMARK OFFICE
CERTIFICATE OF CORRECTION

PATENT NO. : 7,253,315 B2 Page 1 of 1
APPLICATION NO. : 11/088370
DATED : August 7, 2007
INVENTOR(S) : Fu et al.

It is certified that error appears in the above-identified patent and that said Letters Patent is hereby corrected as shown below:

Column 3, line 38, "Light" should read --Heavy-- .

Signed and Sealed this

Sixth Day of November, 2007

JON W. DUDAS
*Director of the United States Patent and Trademark Office*